United States Patent
Zalevsky et al.

(10) Patent No.: US 12,313,916 B2
(45) Date of Patent: May 27, 2025

(54) OPTICAL APPARATUS WITH STRUCTURE FOR LIQUID INVARIANT PERFORMANCE

(71) Applicant: Brien Holden Vision Institute Limited, Sydney (AU)

(72) Inventors: Zeev Zalevsky, Rosh HaAyin (IL); Ofer Limon, Kfar-Saba (IL)

(73) Assignee: Brien Holden Vision Institute Limited, Sydney (AU)

( * ) Notice: Subject to any disclaimer, the term of this patent is extended or adjusted under 35 U.S.C. 154(b) by 0 days.

(21) Appl. No.: 18/373,689

(22) Filed: Sep. 27, 2023

(65) Prior Publication Data
US 2024/0184020 A1   Jun. 6, 2024

Related U.S. Application Data

(63) Continuation of application No. 17/355,800, filed on Jun. 23, 2021, now Pat. No. 11,802,997, which is a
(Continued)

(51) Int. Cl.
*G02C 7/04* (2006.01)
*A61F 2/16* (2006.01)
(Continued)

(52) U.S. Cl.
CPC ............. *G02C 7/022* (2013.01); *A61F 2/16* (2013.01); *A61F 2/1648* (2013.01); *B82Y 20/00* (2013.01);
(Continued)

(58) Field of Classification Search
None
See application file for complete search history.

(56) References Cited

U.S. PATENT DOCUMENTS

| | | |
|---|---|---|
| 3,549,240 A | 12/1970 | Sawatari |
| 4,736,734 A | 4/1988 | Matsuura et al. |

(Continued)

FOREIGN PATENT DOCUMENTS

| | | |
|---|---|---|
| CN | 101510012 | 8/2009 |
| EP | 0369561 | 5/1990 |

(Continued)

OTHER PUBLICATIONS

Kohn, A., Visual Adaptation: physiology, mechanisms, and functional benefits. Journal of Neurophysiol, 2007, 97 (5), pp. 3155-3164.
(Continued)

*Primary Examiner* — Darryl J Collins
(74) *Attorney, Agent, or Firm* — Jones Day

(57) ABSTRACT

A phase-adjusting element configured to provide substantially liquid-invariant extended depth of field for an associated optical lens. One example of a lens incorporating the phase-adjusting element includes the lens having surface with a modulated relief defining a plurality of regions including a first region and a second region, the first region having a depth relative to the second region, and a plurality of nanostructures formed in the first region. The depth of the first region and a spacing between adjacent nanostructures of the plurality of nanostructures is selected to provide a selected average index of refraction of the first region, and the spacing between adjacent nanostructures of the plurality of nanostructures is sufficiently small that the first region does not substantially diffract visible light.

20 Claims, 8 Drawing Sheets

Related U.S. Application Data continuation of application No. 16/028,961, filed on Jul. 6, 2018, now Pat. No. 11,079,517, which is a continuation of application No. 13/578,158, filed as application No. PCT/IL2011/000141 on Feb. 9, 2011, now Pat. No. 10,031,334, which is a continuation-in-part of application No. 12/803,324, filed on Jun. 24, 2010, now Pat. No. 8,169,716.

(60) Provisional application No. 61/302,588, filed on Feb. 9, 2010.

(51) Int. Cl.
| | |
|---|---|
| *B82Y 20/00* | (2011.01) |
| *G02B 3/00* | (2006.01) |
| *G02B 3/08* | (2006.01) |
| *G02B 5/18* | (2006.01) |
| *G02B 27/00* | (2006.01) |
| *G02B 27/42* | (2006.01) |
| *G02C 7/02* | (2006.01) |
| *G02C 7/06* | (2006.01) |

(52) U.S. Cl.
CPC ............. *G02B 3/0081* (2013.01); *G02B 5/18* (2013.01); *G02B 5/1828* (2013.01); *G02B 5/1895* (2013.01); *G02B 27/0025* (2013.01); *G02B 27/0037* (2013.01); *G02B 27/0075* (2013.01); *G02B 27/4205* (2013.01); *G02B 27/4211* (2013.01); *G02C 7/04* (2013.01); *G02C 7/049* (2013.01); *G02C 7/06* (2013.01); *A61F 2/1613* (2013.01); *G02B 3/00* (2013.01); *G02C 2202/22* (2013.01); *Y10S 977/902* (2013.01); *Y10S 977/932* (2013.01)

(56) References Cited

U.S. PATENT DOCUMENTS

| | | | |
|---|---|---|---|
| 4,923,296 | A | 5/1990 | Erickson |
| 4,955,904 | A | 9/1990 | Atebara et al. |
| 5,117,306 | A | 5/1992 | Cohen |
| 5,158,572 | A | 10/1992 | Nielsen |
| 5,172,143 | A | 12/1992 | Baude |
| 5,198,844 | A | 3/1993 | Roffman |
| 5,225,858 | A | 7/1993 | Portney |
| 5,245,367 | A | 9/1993 | Miller et al. |
| 5,260,727 | A | 11/1993 | Oksman et al. |
| 5,299,062 | A | 3/1994 | Ogata |
| 5,302,477 | A | 4/1994 | Dao et al. |
| 5,344,447 | A | 9/1994 | Swanson |
| 5,482,801 | A | 1/1996 | Smith et al. |
| 5,543,966 | A | 8/1996 | Myers |
| 5,662,706 | A | 9/1997 | Legerton et al. |
| 5,674,282 | A | 10/1997 | Cumming |
| 5,674,284 | A | 10/1997 | Cumming |
| 5,682,223 | A | 10/1997 | Menezes et al. |
| 5,715,031 | A | 2/1998 | Roffman et al. |
| 5,748,371 | A | 5/1998 | Cathey et al. |
| 5,757,458 | A | 5/1998 | Miller et al. |
| 5,768,031 | A | 6/1998 | Yang |
| 5,788,883 | A | 8/1998 | Srivastava et al. |
| 5,822,091 | A | 10/1998 | Baker |
| 5,864,379 | A | 1/1999 | Dunn |
| 5,905,561 | A | 5/1999 | Lee et al. |
| 5,965,330 | A | 10/1999 | Evans et al. |
| 5,980,040 | A | 11/1999 | Xu et al. |
| 6,024,447 | A | 2/2000 | Portney |
| 6,069,738 | A | 5/2000 | Cathey et al. |
| 6,097,856 | A | 8/2000 | Hammond |
| 6,172,957 | B1 | 2/2001 | Ogasawara |
| 6,488,798 | B1 | 1/2002 | Sarfarazi |
| 6,451,056 | B1 | 9/2002 | Cumming |
| 6,474,814 | B1 | 11/2002 | Griffin |
| 6,527,389 | B2 | 3/2003 | Portney |
| 6,533,416 | B1 | 3/2003 | Fermigier |
| 6,536,898 | B1 | 3/2003 | Cathey |
| 6,537,317 | B1 | 3/2003 | Steinert et al. |
| 6,554,424 | B1 | 4/2003 | Miller |
| 6,554,859 | B1 | 4/2003 | Lang et al. |
| 6,576,012 | B2 | 6/2003 | Lang |
| 6,661,816 | B2 | 12/2003 | Delfyett et al. |
| 6,685,315 | B1 | 2/2004 | De Carle |
| 7,025,454 | B2 | 4/2006 | Cathey |
| 7,061,693 | B2 | 6/2006 | Zalevsky |
| 7,101,436 | B2 | 9/2006 | Taniguchi et al. |
| 7,224,540 | B2 | 5/2007 | Olmstead et al. |
| 7,365,917 | B2 | 4/2008 | Zalevsky |
| 7,411,743 | B2 | 8/2008 | Sugi |
| 7,569,312 | B2 | 8/2009 | Misaka |
| 7,646,549 | B2 | 1/2010 | Zalevsky et al. |
| 7,859,769 | B2 | 12/2010 | Zalevsky et al. |
| 8,169,716 | B2 | 5/2012 | Zalevsky et al. |
| 8,317,321 | B2 | 11/2012 | Haddock |
| 11,187,921 | B2 | 11/2021 | Zhou et al. |
| 2003/0142268 | A1 | 7/2003 | Miller et al. |
| 2003/0197906 | A1 | 10/2003 | Furuta et al. |
| 2004/0114102 | A1 | 6/2004 | Miller et al. |
| 2004/0114103 | A1 | 6/2004 | Miller et al. |
| 2004/0145808 | A1 | 7/2004 | Cathey |
| 2004/0230299 | A1 | 11/2004 | Simpson |
| 2006/0082882 | A1 | 4/2006 | Wang |
| 2006/0176572 | A1 | 8/2006 | Fiala |
| 2007/0141114 | A1 | 6/2007 | Muisener |
| 2007/0236769 | A1 | 10/2007 | Zalevsky |
| 2008/0198482 | A1 | 8/2008 | Zalevsky |
| 2009/0074239 | A1 | 3/2009 | Zalevsky |
| 2009/0088840 | A1 | 4/2009 | Simpson |
| 2009/0112314 | A1 | 4/2009 | Sarver |
| 2009/0116096 | A1 | 5/2009 | Zalevsky et al. |
| 2009/0147378 | A1 | 6/2009 | Zalevsky |
| 2009/0187242 | A1 | 7/2009 | Weeber |
| 2009/0234448 | A1 | 9/2009 | Weeber |
| 2009/0303432 | A1 | 12/2009 | Suzuki |
| 2010/0075114 | A1 | 3/2010 | Kurihara et al. |
| 2010/0097569 | A1 | 4/2010 | Weeber |
| 2010/0149510 | A1 | 6/2010 | Zaczek et al. |
| 2011/0051080 | A1 | 3/2011 | Bandhauer |
| 2011/0082541 | A1 | 4/2011 | Zalevsky |
| 2012/0140166 | A1 | 6/2012 | Zhao |
| 2012/0165932 | A1 | 6/2012 | Argal |

FOREIGN PATENT DOCUMENTS

| | | |
|---|---|---|
| JP | 2137815 | 5/1990 |
| WO | WO199957599 | 11/1999 |
| WO | WO200135880 | 5/2001 |
| WO | WO2003012528 | 2/2003 |
| WO | WO2003032825 | 4/2003 |
| WO | WO2003052465 | 6/2003 |
| WO | WO2003052492 | 6/2003 |
| WO | WO2003076984 | 9/2003 |
| WO | WO2004113994 | 12/2004 |
| WO | WO2007141788 | 12/2007 |
| WO | WO2009115932 | 9/2009 |
| WO | WO2009140080 | 11/2009 |
| WO | WO2010009254 | 1/2010 |

OTHER PUBLICATIONS

Webster, M.A. Georgeson, M.A., and Webster, S.M., "Neural adjustments to image blur". Nat Neurosci, 2002, 5 (9), pp. 839-840, Unites States—abstract only.

Pesudovs, K., & Brennan, N.A., Decreased uncorrected vision after a period of distance fixation with spectacle wear, Optom Vis Sci, 1993, pp. 528-531, 70 (7), United States—abstract only.

Yehezkel O., Belkin M., Sagi D. & Polat U., Adaptation to astigmatic lens: effects on lateral interaction, Visual Sciences Society Annual Meeting, 2005—abstract only.

Webster, M. Sawides, L., Ravikumar, S., Thibos, L., Bradley, A. & Marcos, S., Adapting to astigmatism. Journal of Vision, 2009, pp. 986, 986a, 9)8)—abstract only.

(56) References Cited

OTHER PUBLICATIONS

Forrest, E.B., Eye Scan Therapy for Astigmatism, Journal of the American Optometric Association, 1984, pp. 894-901, 55(12)—abstract only.
T. Callina and T.P. Reynolds, "Traditional methods for the treatment of presbyopia: spectacles, contact lenses, bifocal contact lenses", Ophthalmology Clinics of North America, 2006, pp. 25-33 19(1)—abstract only.
C.W. Fowler and E.S. Pateras, "A gradient-index ophthalmic lens based on Wood's convex pseudo-lens, " Ophthalmic and Physiological Optic, 1990, pp. 262-270 10(3),—abstract only.
C.M. Sullivan and C.W. Fowler, "Progressive addition and variable focus lenses: a review, "Ophthalmic and Physiological Optics, 1986, pp. 401-414, 8(4),—abstract only.
Di Feng, Pan Ou, Li-Shuang Feng, Shu-Ling Hu, and Chun-Xi Zhang, "Binary sub-wavelength diffractive lenses with long focal depth and high transverse resolution, "Opt. Express, 2008, pp. 20968-20973 16, Unites States.
Joseph N. Mait, Axel Scherer, Oliver Dial, Dennis W. Prather, and Xiang Gao, "Diffractive lens fabricated with binary features less than 60mm, "Opt. Lett, 2000, pp. 381-383, 25, United States.
Michael W. Farn, "Binary Gratings with increased efficiency," Appl. Opt., 1992, pp. 4453-4458, 31, United States.
Petit, R., and G. Bouchitt E, "Replacement of a very fine grating by a stratified layer: homogenization techniques and the multiple scale method," SPIE Proceedings Application and Theory of Period Structures, Diffraction Grating, and Moir'e Phenomena 431, 19987, vol. 815, ed. J. Lerner, France.
Yehezkel, O. Sagi, D. Sterkin, A., Belkin, M. & Polat, U., Learning to adapt: Dynamics of readaptation to geometrical distortions, Vision Research, 2010, pp. 1550-1558, 50, Israel.
Zalevsky et al., "All-optical axial super resolving imaging using a low-frequency binary-phase mask" Optics Express, OSA (Optical Society of America), Apr. 3, 2006, pp. 2631-2643, vol. 14. No. 7, Washington DC, United States.
Sales, T R M et al., "Diffractive supperresolution elements", Journal of the optical society of America, Jul. 1997, pp. 1637-1646; vol. 14, No. 7, United States.
De Juana D M et al, "Focusing properties of annular binary phase filters", Optics communications, Jan. 2, 2004, pp. 71-77, vol. 229, No. 1-6, North-Holland Publishing Co., Amsterdam, NL.
Bradurn, S. et al., "Realizations of focus invariance in optical-digital systems with wave-front coding", Applied Optics. OSA, Optical Society of America, Dec. 10, 1997, pp. 9157-9166, vol. 36, No. 35, Unites States.
L.A. Carvalho, "A Simple mathematical model for simulation of the human optical system based on in vivo corneal data," Revista Brasileira de Engenharia Biomedica, 2003, 19, pp. 29-37, Brazil.
Fitzgerrell, A R et al: "Defocus transfer function for circularly symmetric pupils", Applied Optics OPT. Soc. America, Aug. 10, 1997, pp. 5796-5804, vol. 36., No. 23, United States.
Hecht, Eugene, "Optik" Dec. 31, 1989, pp. 441-445, Addison-Wesley Publishing Company, Bonn, Munchen, Germany.
Varamit, C et al., "Imaging properties of defocused partitioned pupils" Journal of the Optical Society of America (Optics and Image Science), Jun. 1985, pp. 799-802, vol. 2, No. 6, United States.
H. Wang & F. Gan, "High focal depth with pure-phase apodizer", Applied Optics, Nov. 1, 2001, pp. 5658-5662, vol. 40, No. 31, United States.

OPTICAL APPARATUS WITH STRUCTURE FOR LIQUID INVARIANT PERFORMANCE

CROSS REFERENCE TO RELATED APPLICATION

This application is a continuation of U.S. patent application Ser. No. 17/355,800, filed Jun. 23, 2021, which is a continuation of U.S. patent application Ser. No. 16/028,961, filed Jul. 6, 2018, now U.S. Pat. No. 11,079,517, which is a continuation of U.S. application Ser. No. 13/578,158, filed Oct. 23, 2012, now U.S. Pat. No. 10,031,334, which is the National Phase application of International Application No. PCT/IL2011/000141, filed Feb. 9, 2011, which designates the United States and published in English, and which is further a continuation-in-part of U.S. patent application Ser. No. 12/803,324, filed Jun. 24, 2010, now U.S. Pat. No. 8,169,716, and further claims priority to U.S. Provisional Application No. 61/302,588, filed Feb. 9, 2010. The foregoing related applications, in their entirety, are incorporated herein by reference.

FIELD AND BACKGROUND

The present invention relates generally optical systems and apparatus, in particular, to optical lenses having extended depth of field.

Several approaches have been developed for obtaining extended depth of field of an optical apparatus. Recent technologies involving extended depth of field for various optical applications, including ophthalmic applications, are using annular grooves across a standard lens to create a phase retardation that leads to an interference pattern along the focal distance which, when controlled properly, can provide an extended depth of field. An example of this approach is described in U.S. Pat. No. 7,365,917, which is incorporated herein by reference in its entirety. Other techniques for extending the depth of field include presenting diffractional optic elements that can diffract the optical signal into different diffraction orders thereby realizing a bi-focal or multi-focal lens that allows a clear vision for different object distances using a single passive lens. Both technologies implement phase reshaping by introducing a lateral (i.e., along the surface of the lens) geometrical lens reshaping that produces the required phase retardation along a few microns in the longitudinal axis of the lens.

GENERAL DESCRIPTION

Aspects and embodiments are directed to a phase-adjusting element configured to provide extended depth of field for an associated optical lens in an environment where liquid may be present. In particular, aspects and embodiments are directed to a phase-adjusting element that operates in essentially the same manner despite the presence of liquid in the surrounding environment, and/or is configured to account for the presence of liquid, and which therefore may provide a substantially liquid-invariant extended depth of field for the associated optical lens, as discussed further below.

According to one embodiment, a lens comprises a surface having a modulated relief comprising a first region and a second region, the first region having a predetermined depth relative to the second region, and a plurality of nanostructures formed in the first region, and wherein the spacing between adjacent nanostructures of the plurality of nanostructures is sufficiently small such that the first region does not substantially diffract visible light. In one example, the depth of the first region and a spacing between adjacent nanostructures of the plurality of nanostructures is selected to provide a predetermined average index of refraction of the first region.

In one example of the lens, the plurality of nanostructures extend away from a base of the first region. In one example, the spacing between adjacent nanostructures of the plurality of nanostructures is less than approximately a shortest wavelength of visible light in free space. In another example, the spacing between adjacent nanostructures of the plurality of nanostructures is less than approximately 400 nanometers. Each nanostructure of the plurality of nanostructures may have a height that is less than or equal to the depth of the first region. The first region may include, for example, a circular region, an annular region, or a plurality of concentric regions. In one example, the nanostructures are uniformly spaced apart from one another. In another example, the spacing between the adjacent nanostructures decreases from a largest spacing at a center of the first region to smallest spacing at edges of the first region. In another example, the spacing between the adjacent nanostructures is sufficiently small to prevent water from penetrating between the nanostructures at atmospheric pressure. The lens may be, for example, an ophthalmic contact lens, an intraocular lens, a spectacle lens, or any of numerous other types of optical lenses.

According to another embodiment, a lens having a depth of field comprises a phase-adjusting region formed in a lens surface of the lens, the phase-adjusting region extending into the lens by a depth and configured to extend the depth of field of the lens, and a plurality of nanostructures formed in the phase-adjusting region, the plurality of nanostructures extending away from a base of the phase-adjusting region, wherein a spacing between adjacent nanostructures of the plurality of nanostructures is less than approximately 400 nanometers.

In one example of the lens, each nanostructure of the plurality of nanostructures has a height that is less than or equal to the depth of the phase-adjusting region. The phase-adjusting region may be, for example, a circular region or an annular region. In one example, lens further comprises at least one additional phase-adjusting region, and at least one corresponding additional plurality of nanostructures formed in the at least one additional phase-adjusting region. In one example, the nanostructures are uniformly spaced apart from one another. In another example, the spacing between the adjacent nanostructures decreases from a largest spacing at a center of the phase-adjusting region to smallest spacing at edges of the phase-adjusting region. In another example, the spacing between the adjacent nanostructures is sufficiently small so as to prevent water from penetrating between the nanostructures at atmospheric pressure. A density of the plurality of nanostructures and the depth of the phase-adjusting region may be selected based at least in part on a predetermined desired average refractive index of the phase-adjusting region. The lens may be an ophthalmic contact lens, or any of numerous other types of optical lenses, as discussed above.

According to another embodiment, an imaging apparatus comprises a lens and a phase-adjusting optical element associated with the lens and configured to extend a depth of field of the lens, the phase-adjusting optical element comprising a plurality of nanostructures, wherein a spacing between adjacent nanostructures of the plurality of nanostructures is less than approximately 400 nanometers. The imaging apparatus may further comprises a detector optically coupled to the lens and configured to detect light passing through the lens, and a processor coupled to the detector and configured to produce an image from the light detected by the detector. The imaging apparatus may be, for example, a camera.

In one example of the imaging apparatus, the phase-adjusting optical element comprises a surface relief on the lens including at least one first region and at least one second region, the at least one first region being recessed relative to the at least one second region, wherein the plurality of nanostructures are formed in the at least one first region and extend away from a base of the at least one first region. Each nanostructure of the plurality of nanostructures has a height that may be less than or equal to a depth of the at least one first region. In one example, a density of the plurality of nanostructures and a depth of the at least one first region are selected based at least in part on a predetermined desired average refractive index of the first region. In another example, the phase-adjusting optical element comprises a surface relief on the lens defining a plurality of recessed regions, and a corresponding plurality of groups of nanostructures, each group of nanostructures formed in a respective one of the plurality of recessed regions. The recessed regions may have any of numerous different geometric or non-geometric shapes. In one example, the plurality of recessed regions comprises a plurality of concentric annular regions. In another example, the phase-adjusting optical element comprises a surface relief on the lens defining either an annular region or a circular region, wherein the plurality of nanostructures are formed in the annular or circular region and extend away from a base of the annular or circular region.

Another embodiment is directed to a method of extending a depth of field of a lens, the method comprising forming a phase-adjusting region in a surface of the lens, the phase-adjusting region extending into the lens by a predetermined depth, and forming a plurality of nanostructures in the phase-adjusting region, the plurality of nanostructures having a density selected to provide a predetermined average index of refraction for the phase-adjusting region.

In one example of the method, forming the phase-adjusting region and forming the plurality of nanostructures include etching the surface of the lens in the phase-adjusting region, and forming the phase-adjusting region and forming the plurality of nanostructures are performed simultaneously. The method may further comprise masking the surface of the lens with a pattern of the plurality of nanostructures prior to etching the surface of the lens. In one example, forming the plurality of nanostructures includes forming a uniformly spaced plurality of nanostructures. In another example, forming the plurality of nanostructures includes forming a non-uniformly spaced plurality of nanostructures. Forming the phase-adjusting region may include forming one of a circular region and an annular region in the surface of the lens.

Still other aspects, embodiments, and advantages of these exemplary aspects and embodiments, are discussed in detail below. Any embodiment disclosed herein may be combined with any other embodiment in any manner consistent with at least one of the objects, aims, and needs disclosed herein, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. The appearances of such terms herein are not necessarily all referring to the same embodiment. The accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments

BRIEF DESCRIPTION OF THE DRAWINGS

Various aspects of at least one embodiment are discussed below with reference to the accompanying figures, which are not intended to be drawn to scale. Where technical features in the figures, detailed description or any claim are followed by references signs, the reference signs have been included for the sole purpose of increasing the intelligibility of the figures, detailed description, and claims. Accordingly, neither the reference signs nor their absence are intended to have any limiting effect on the scope of any claim elements. In the figures, each identical or nearly identical component that is illustrated in various figures is represented by a like numeral. For purposes of clarity, not every component may be labeled in every figure. The figures are provided for the purposes of illustration and explanation and are not intended as a definition of the limits of the invention. In the figures:

DETAILED DESCRIPTION

Figure 1:
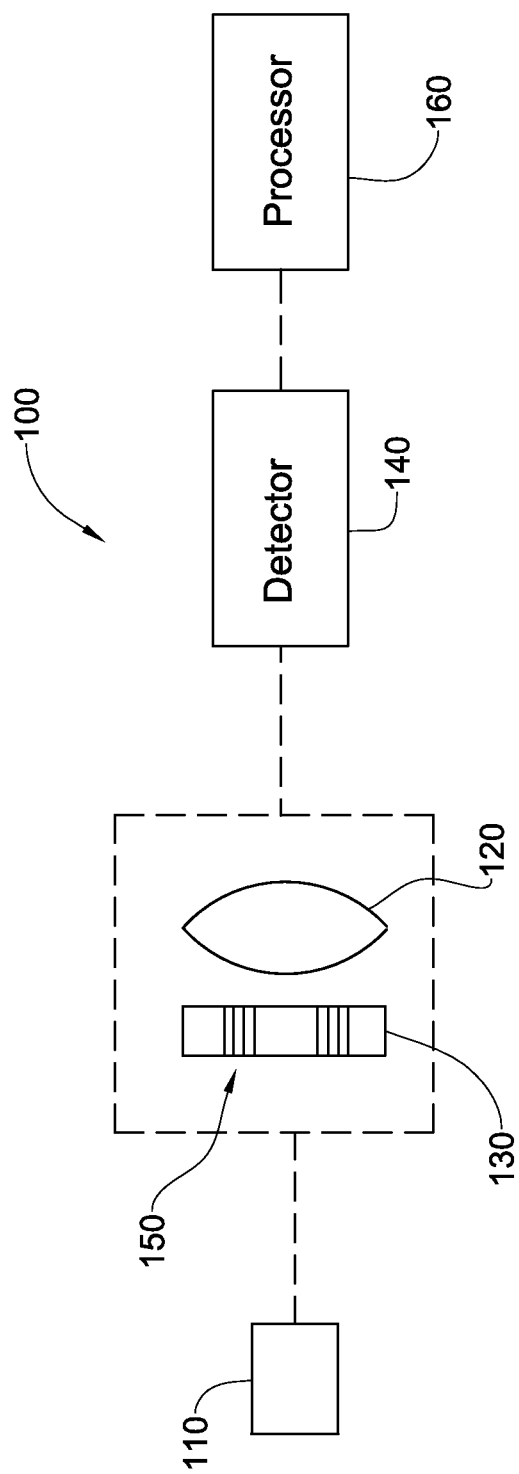
FIG. 1 is a block diagram of one example of an imaging apparatus according to aspects of the invention.

As discussed above, several technologies for extending the depth of field of a lens implement a phase-adjusting element to reshape the phase of the optical signal passing though the lens, thereby achieving an extended depth of field. To maintain accurate phase reshaping, the refractive index difference between the phase-adjusting element and its surroundings must be controlled with high precision. In liquid environments, however, the presence of the liquid in the phase-adjusting element can significantly alter the refractive index of the element. For example, in ophthalmic applications the variable presence of tears in the eyes can create a large uncertainty with respect to the refractive index of the space surrounding the phase-adjusting element at any given time. Aspects and embodiments are directed to a phase-adjusting element having a structure that provides liquid-invariant performance of the phase-adjusting element. In one embodiment, the phase-adjusting element includes at least one region having an array of nanostructures formed therein. The region(s) produce a phase retardation in the longitudinal axis of the lens (i.e. along an optical axis of the lens) to achieve extended depth of field for the lens, and the nanostructures inhibit micro fluidic movement within the phase-adjusting element to provide liquid-invariant phase reshaping, as discussed further below.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiments.

Also, the phraseology and terminology used herein is for the purpose of description and should not be regarded as limiting. Any references to embodiments or elements or acts of the systems and methods herein referred to in the singular may also embrace embodiments including a plurality of these elements, and any references in plural to any embodiment or element or act herein may also embrace embodiments including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

Referring to FIG. 1, there is illustrated a block diagram of an imaging apparatus 100 according to one embodiment which is configured to image an object 110. The imaging apparatus 100 includes a lens 120, a phase-adjusting element 130, and a detector 140, and may also include a processor 160 configured to process images from the light detected by the detector 140. The phase-adjusting element 130 is configured to provide liquid-invariant extended depth of field for the lens 120, as discussed further below. The phase-adjusting element 130 may be a separate element attached to the lens 120 or located close thereto, or may be implemented integral with the lens 120, for example as a surface relief on the lens as discussed further below. For example, the phase-adjusting element 130 may include a pattern of spaced apart, optically transparent regions 150 that have a different refractive index and/or different thickness compared to other regions of phase-adjusting element and/or lens and thus affect the phase of the light passing therethrough. The phase differences caused by the region(s) 150 are small, for example, less than π. In order to extend the depth of field of the lens 120, the phase differences caused by the region(s) 150 are designed to create a constructive/destructive interference pattern of the light passing through the phase-adjusting element. If a liquid enters the region(s) 150, the refractive index of the region will change, and therefore the phase difference will change as well, resulting in a change in the interference pattern caused by the phase-adjusting element 130. To avoid this situation, according to one embodiment, the region(s) 150 of the phase-adjusting element 130 are "roughened" to prevent liquid from entering the region(s); thereby improving the robustness of the extended depth of field of the lens 120 in environments where liquid may be present.

The imaging apparatus 100 may be used in a wide variety of equipment and applications, such as, for example, cameras, machine vision applications, photography, television systems, video conference systems, radar imaging systems, endoscopy and passive bio-medical inspections, tomography, display panels, etc. Embodiments of the imaging apparatus may also be used in ophthalmic applications, such as a contact lens, a spectacle lens, an intraocular lens, or any other lens used around or inserted into any part of the eye. In these applications, the detector 140 may be the retina and the processor 160 may include part of the brain.

Figure 2A:
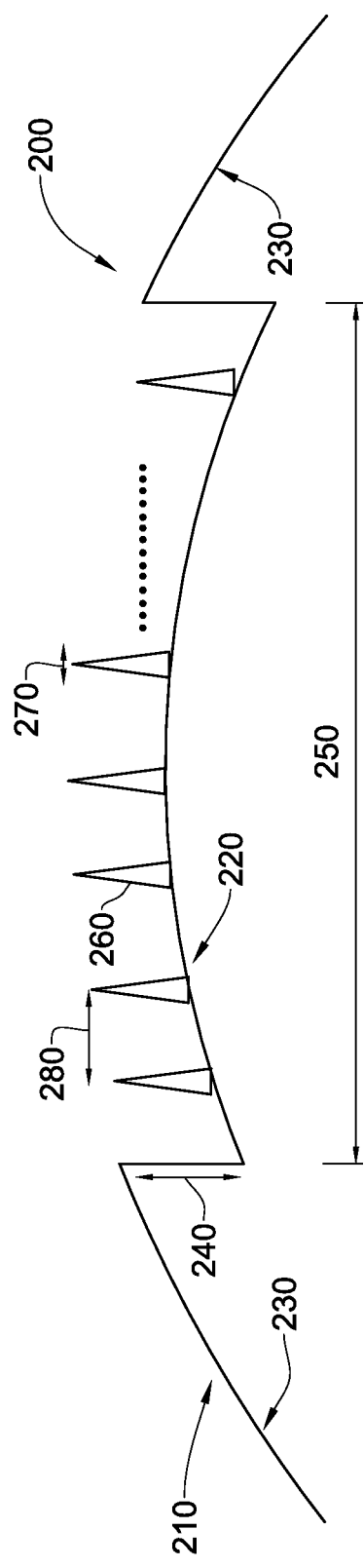
FIG. 2A is a diagram of one example of a lens including a phase-adjusting element according to aspects of the invention.

As discussed above, according to one embodiment, the phase-adjusting element 130 is implemented integral with the lens 120. Accordingly, referring to FIG. 2A, there is illustrated a diagram of a lens 200 including a phase-adjusting element according to one embodiment. The lens 200 has a surface 210 which has a modulated relief thereby comprising a plurality of regions including a first region 220 and a second region 230. The first region 220 being recessed and having a depth 240 relative to the second region 230. A plurality of nanostructures 260 are formed in the first region 220, extending upward from the base of the first region, as illustrated in FIG. 2A. The phase-adjusting element 130 comprises the combination of the modulated lens surface 210 and the plurality of nanostructures 260. As used herein, the term "nanostructure" is intended to refer to a structure of intermediate size between molecular and microscopic (micrometer-sized), and which is small relative to the size of the overall object in which it is formed. The term "nanostructure" as used herein does not require the structure to be smaller than 100 nanometers in a given dimension.

Referring to FIG. 2A, the first region 220 has a lateral width 250 that is at least one wavelength at the lower (red) end of the visible spectrum. In one example, the lateral width 250 of the first region is large compared to the wavelengths of visible light, for example, at least several wavelengths at the lower end of the visible spectrum. Thus, the surface relief of the lens 200 does not cause diffraction of visible light passing through the phase-adjusting element because the surface relief is laterally large compared to the wavelengths of visible light. The nanostructures 260 each have a lateral width 270 and are spaced apart from one another by a spacing 280. This spacing 280 may be made small such that the light wave is substantially unaffected other than to see change in the average index of refraction of the first region. The spacing 280 may be selected based on at least the following factors. First, the spacing 280 is less than approximately one wavelength at the higher (blue) end of the visible light spectrum to avoid scattering diffraction and prevent generation of undesired diffraction orders. Second, as discussed further below, the density of the nanostructures (determined by the spacing 280) and the depth 240 of the first region 220 are selected to provide a desired average index of refraction for the first region. In addition, the spacing 280 is selected to prevent micro fluidic movement in the first region 220, as also discussed further below. The height of the nanostructures 260 may be up to approximately the depth 240. In one embodiment, the depth 240 of the first region 220 is small, for example, less than the optical wavelength.

According to one embodiment, the array of nanostructures 260 forms a binary grating that has an average index of refraction. Because the spacing 280 between the nanostructures 260 is smaller than the optical wavelength, the array of nanostructures does not diffract visible light; instead the light "sees" the first region 220 as a whole having an average index of refraction, determined by the material of the nanostructures and the interstitial substance (e.g., the surrounding liquid or air), rather than an array of distinct nanostructures. As a result, the phase-adjusting element is not diffractive to visible light passing therethrough; instead substantially all the light remains in the zeroth order. Accordingly, the phase-adjusting element may be termed "non-diffractive" to visible light. In one embodiment, the phase-adjusting element is also not refractive in that it does not provide optical power. It is to be appreciated that although in one embodiment the phase-adjusting element is not refractive, the associated optical lens 200 may be refractive. As used herein, the term "non-diffractive" is intended to mean a structure that may be not diffractive (as described above) and also not refractive (as described above).

The phase-adjusting element 130 may be formed using any of a variety of techniques, depending for example on the material of the lens 200 and whether or not the phase-adjusting element 130 is integral with the lens or a separate element. For example, the phase-adjusting element may be formed by selectively etching the lens surface 210 to create the modulated relief and array of nanostructures. In this example, the nanostructures 260 may be formed simultaneously with the pattern of the surface relief, and are made of the same material as the lens itself. The etching process may be a chemical etching process or a mechanical etching process. In another example, the nanostructures may be formed using a deposition process to deposit or "grow" the nanostructures on the surface 210 of the lens 200, in which case the nanostructures may comprise the same material as the lens or a different material.

Figure 2B:
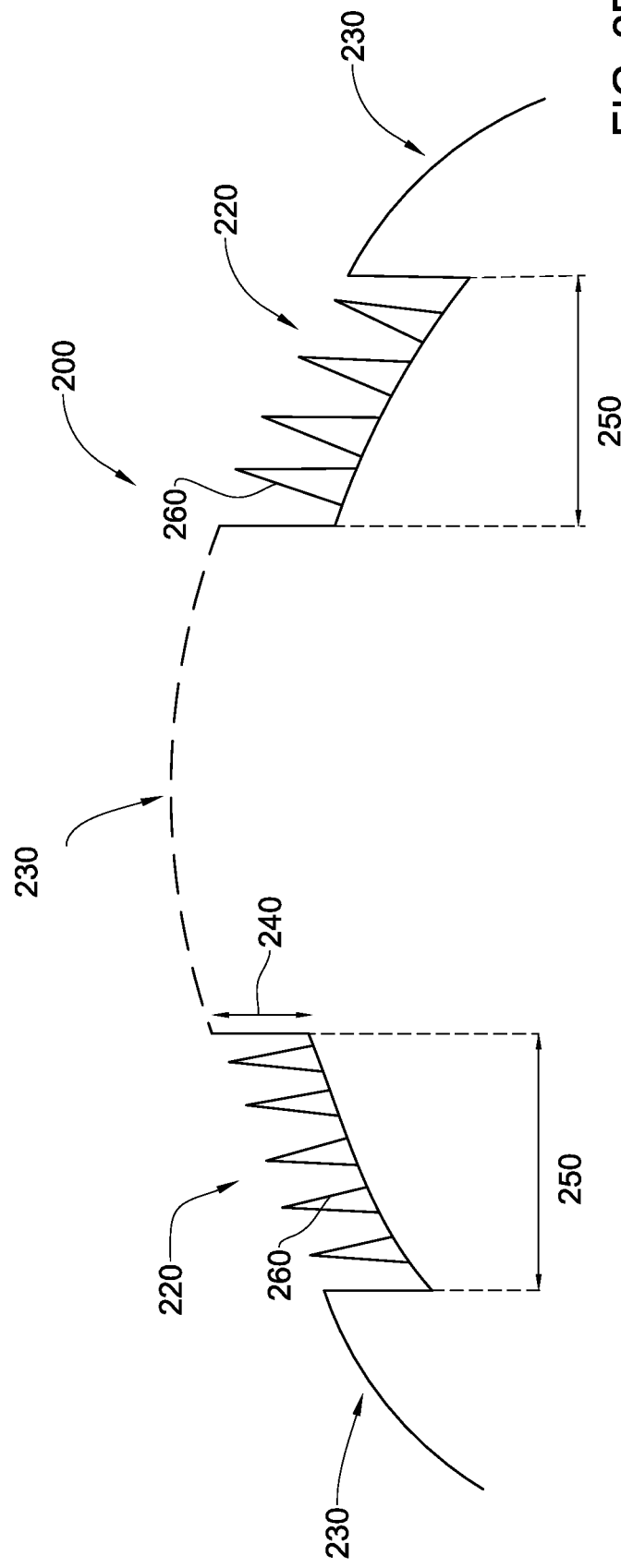
FIG. 2B is a diagram of another example of a lens including a phase-adjusting element according to aspects of the invention.
Figures 3A, 3B:
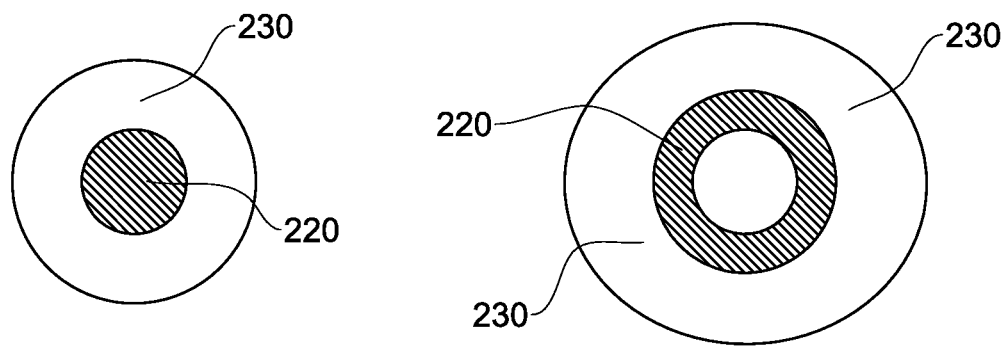
FIG. 3A is a schematic plan view of the lens of FIG. 2A.
FIG. 3B is a schematic plan view of the lens of FIG. 2B.

In the example illustrated in FIG. 2A, the first region 220 is an approximately circular region formed in the surface of the lens 200, as illustrated in FIG. 3B. However, it is to be appreciated that the first region 220 may assume numerous shapes, not limited to the example illustrated in FIGS. 2A and 3A. For example, referring to FIG. 2B there is illustrated another example of a lens 200 in which the first region 220 is an annular region (as illustrated in FIG. 3B). The first region 220 may also assume numerous other shapes, such as, but not limited to, rectangular, square, and other geometric or non-geometric shapes of the same lateral width or different lateral widths. In addition, although FIG. 2A illustrates a single first region 220, the phase-adjusting element may include multiple first regions 220, and multiple second regions 230, and is not limited to a single first region or single second region. For example, the first region 220 may comprise a series of concentric annular regions, optionally including a central substantially circular region, with a second region 230 disposed between each adjacent pair of concentric first regions. In addition, the shape of the first region 220 may vary depending on the shape of the lens 200. Furthermore, the shape of the nanostructures is not limited to the triangular shape illustrated in FIGS. 2A and 2B. The nanostructures may have any of a variety of shapes, which may depend (at least in part) on the manufacturing process used to form the nanostructures, and which may include, for example, rectangular, dome, cylindrical or random shapes.

The phase retardation caused by the first region 220 depends on the average index of refraction of the region, which is determined by the depth 240 and the density of the nanostructures 260. The depth 240 can be calculated according to the following equation:

$$\delta = \frac{\Delta\phi_d \lambda_0}{2\pi(n - n_{\mathit{eff}})} \tag{1}$$

In equation (1), $\delta$ is the depth 240, $\lambda_0$ is the nominal wavelength of the light, n is the refractive index of the lens, $n_{\mathit{eff}}$ is the average refractive index of the first region 220, given by equation (2) below, and $\Delta\phi_d$ is the desired phase retardation that the first region 220 is configured to provide.

$$n_{\mathit{eff}} = \frac{\Delta x \cdot M \cdot n + (L - \Delta x \cdot M)}{L} \tag{2}$$

In equation (2), $\Delta x$ is the average width 270 of the nanostructures 260, M is the number of nanostructures in the first region 220, and L is the lateral width 250 of the first region 220. Accordingly, the depth 240 of the first region 220 can be calculated based on a known desired phase retardation and a known average index of refraction of the first region, and the average index of refraction can be determined based on a known lateral width 250 of the first region and the size and density of the nanostructures 260 within the first region.

Any of the above-mentioned parameters may be varied, subject to certain constraints (such as, for example, manufacturing capability, and suitable materials for the lens, optical constraints, etc.) to achieve a structure for the phase-adjusting element that achieves a desired phase retardation and therefore a desired interference pattern to extend the depth of field of the lens 200. One optical constraint is the density of the nanostructures 260. In particular, the spacing 280 between the nanostructures 260 may be less than approximately the nominal optical wavelength $\lambda_0$ to avoid generating undesired diffraction orders. In one example, the spacing 280 between the nanostructures 260 is less than 400 nanometers (nm), for example, in a range of approximately 300 nm to 400 nm. The spacing 280 may be made smaller than the shortest wavelength in the visible spectrum such that the phase-adjusting element is non-diffractive to visible light. The nanostructures 260 may be made nearly adjacent, particularly as advances in modern chemical processing techniques have made it possible to achieve a very dense structure with good repeatability; however, as the density of the nanostructures in the first region 220 increases, the average refractive index of the first region also increases. Therefore, to maintain a given average refractive index, for a denser array of nanostructures 260, the depth 240 of the first region 220 may be increased, according to equations (1) and (2) given above. In one example, a depth 240 of approximately 1 micrometer (μm) to approximately 1.5 μm is presently practical for ophthalmic contact lenses.

According to one embodiment, the nanostructures 260 are sufficiently closely spaced to create a surface tension that is greater than the pressure of the liquid; hence the array of nanostructures will maintain a steady state environment within the first region 220 even in the presence of the liquid. For example, for ophthalmic contact lenses, the nanostructures may be sufficiently closely spaced to prevent tears from entering the first region 220 at approximately atmospheric pressure (experienced at or near the Earth's surface). The lens 200 including the phase-adjusting element can be configured to account for two steady state conditions in which micro fluidics movement inside the first region 220 is substantially prevented. In the first configuration, the array of nanostructures 260 prevents liquids from penetrating the first region 220 between the nanostructures in a hydrophobic material. In the second configuration, the nanostructure 260 are either made from a hydrophilic material or such a material is provided in the space between the nanostructures 260 of the first region 220 such that the space between these nanostructures is constantly filled with the surrounding liquid. The configuration of the lens 200 may be selected based on an expected environment in which the lens is to be used. For example, in environments where liquid is only sporadically present, the first configuration may be preferred. The following simulations, which demonstrate performance of an example of the lens 200 including an embodiment of the phase-adjusting element, assume a hydrophilic material and therefore demonstrate performance of the structure for the more severe diffraction case since the wavelength of the light is shorter due to the presence of the liquid.

An example of the phase-adjusting element 130 including a nanostructure array was simulated using Comsol Multiphysics, a modeling and simulation program available from the COMSOL Group, to solve Maxwell's wave equation via the finite element method. A reference phase-adjusting element, including recessed region without any nanostructure array, was also simulated to provide reference data with which to compare the simulation results obtained for the example phase-adjusting element 130. For both simulations, the illumination was a normally incident TE polarized plane wave having a wavelength $\lambda_0$ of 550 nm in free space.

Figure 4:
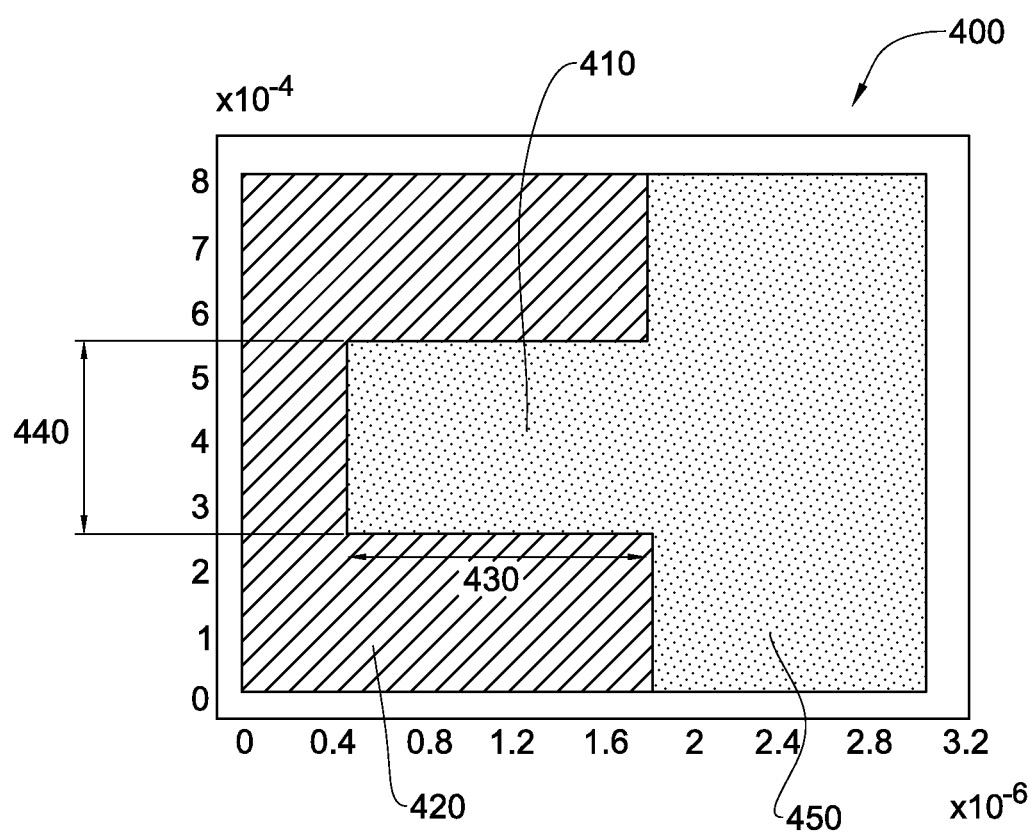
FIG. 4 is a diagram of a simulated reference phase-adjusting element.

A diagram of the simulated reference element 400 is illustrated in FIG. 4. The reference element has a recessed region 410, corresponding to the first region 220 of lens 200 in FIG. 2A, formed in a surrounding material 420. The recessed region 410 has a width 440 of 300 μm and a depth 430 (δ) that matches the π condition of equation (3):

$$\delta = \frac{\lambda_0}{2\Delta n} \quad (3)$$

In equation (3), Δn is the difference between the refractive index of the surrounding material 420 and the refractive index of the environment 450. For the simulations, the surrounding material is specified as BK7 optical glass having a refractive index of 1.517, and the environment 450 is specified as water having a refractive index of 1.3. Accordingly, from equation (3), the recessed region had a depth δ=1.267 μm. The total width of the simulated structure is 0.8 millimeters (mm) and the length (in the dimension of the depth 450) is 3.5 μm.

Figure 5:
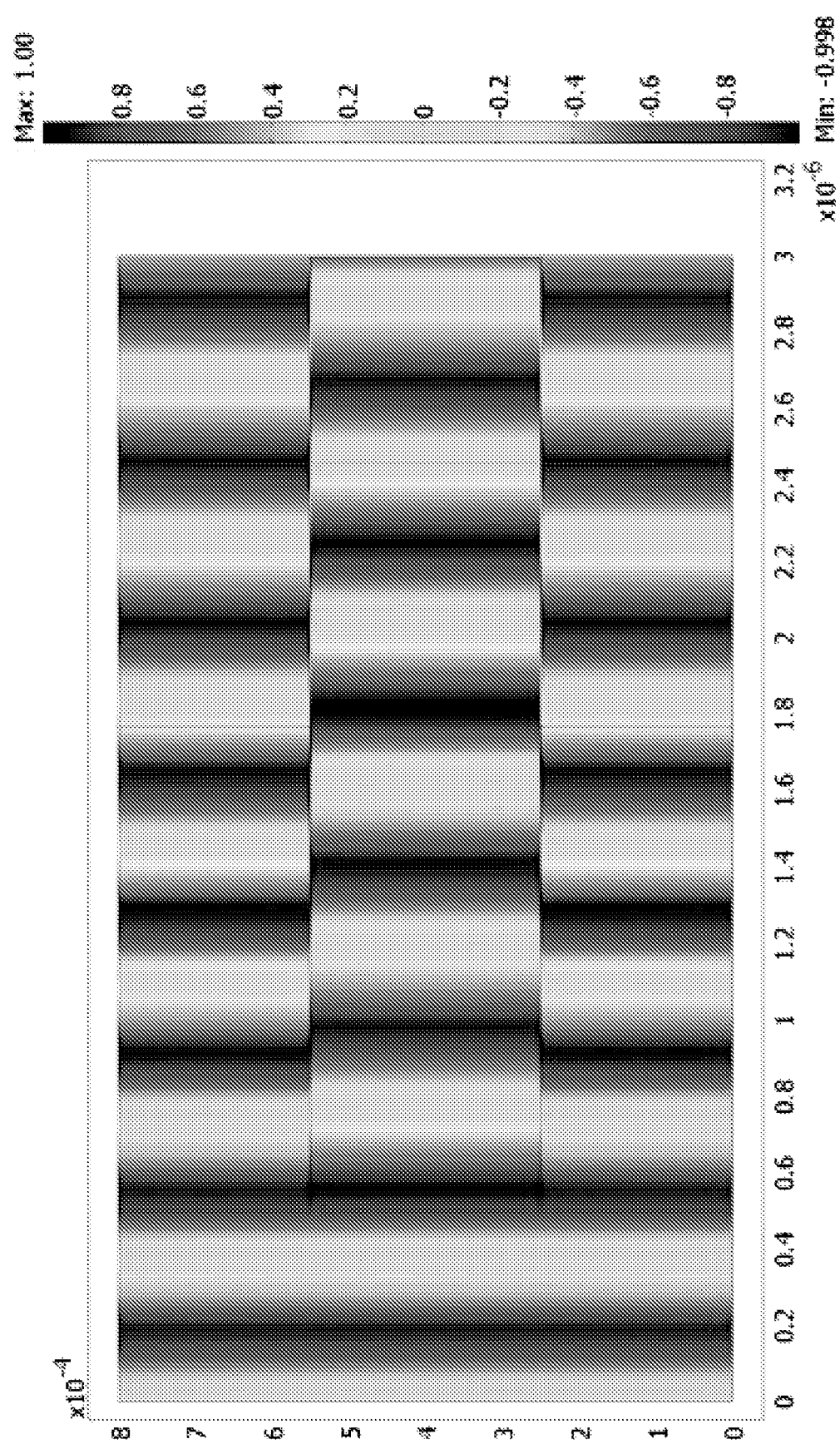
FIG. 5 is a diagram of the phase distribution of the perpendicular electric field along the simulated reference element of FIG. 4.

Referring to FIG. 5 there is illustrated the simulated phase distribution of the perpendicular electric field along the reference element 400 of FIG. 4. FIG. 5 demonstrates that the phase difference between the recessed region 410 and the surrounding material 420 is linearly summed along depth the recessed region 410 with a phase delay of π generated at the end of the 1.267 μm recessed region. Thus, the reference element 400 implements an inverting phase plate.

Figure 6A:
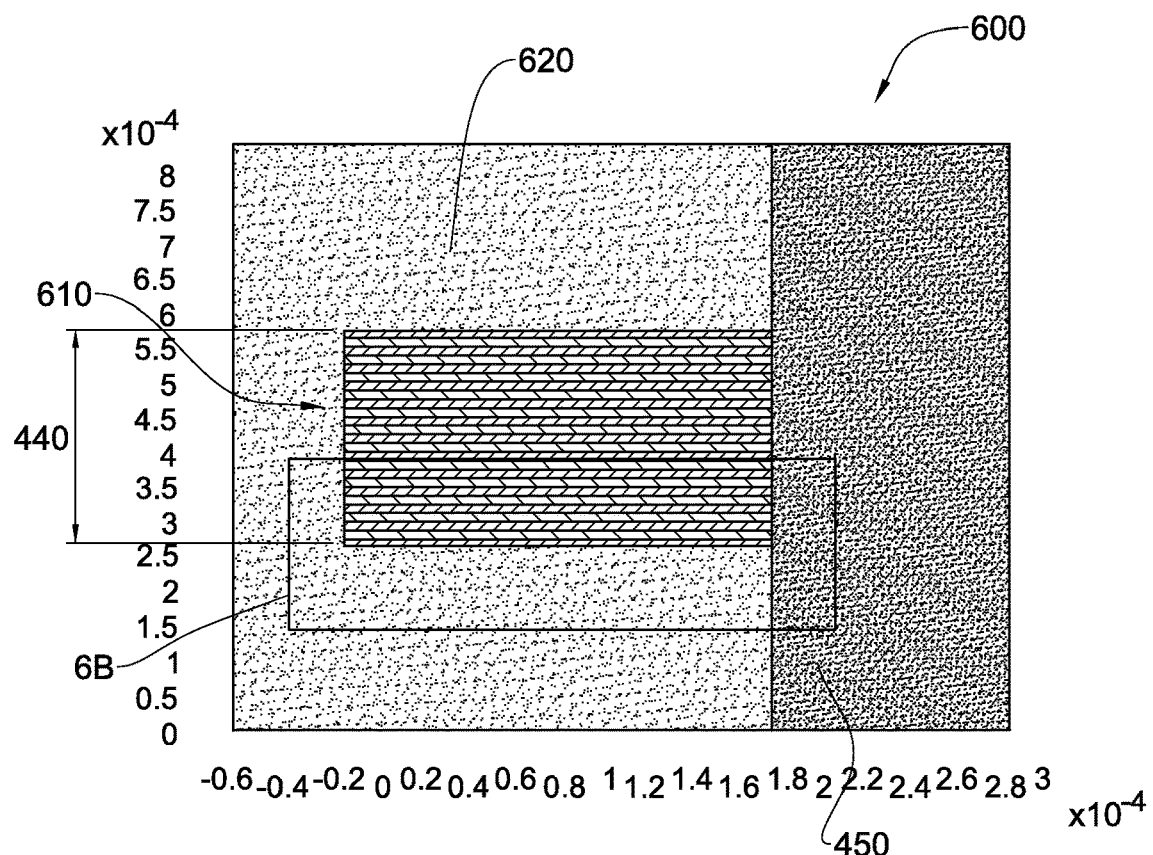
FIG. 6A is a diagram of a simulated example of a phase-adjusting element including an array of nanostructures according to aspects of the invention.
Figure 6B:
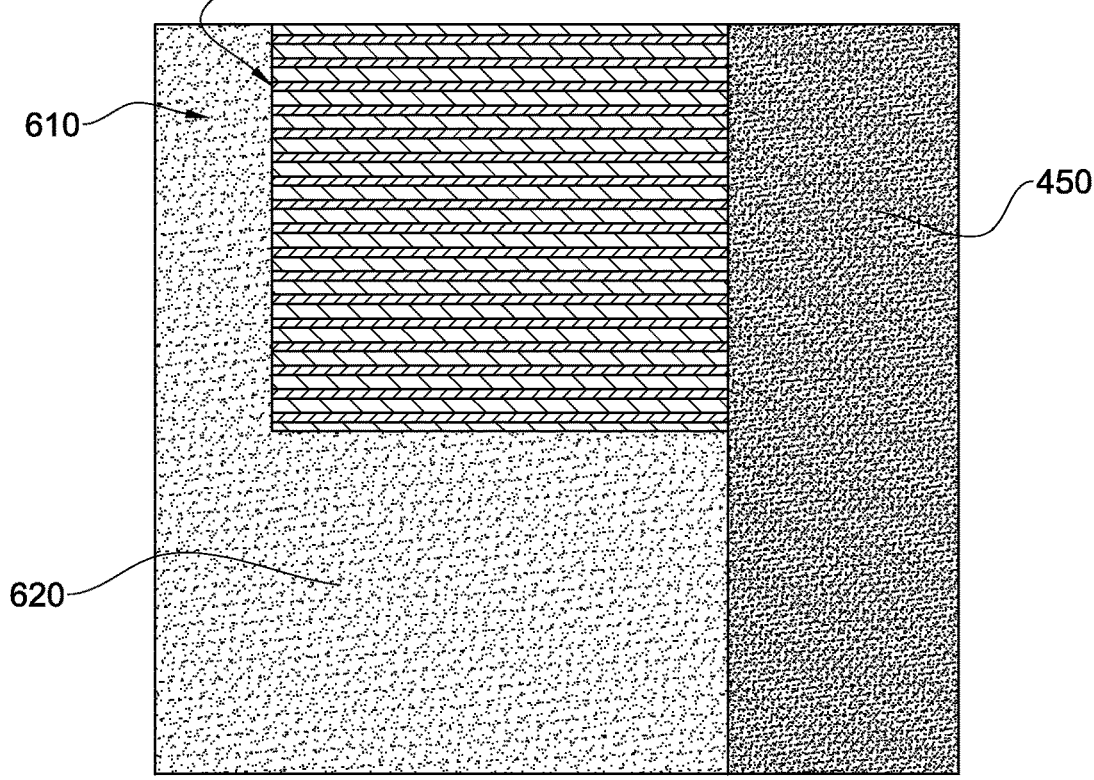
FIG. 6B is an enlarged view of the portion of FIG. 6A contained in box 6B in FIG. 6A, illustrating the simulated nanostructures according to aspects of the invention.

Referring to FIG. 6A there is illustrated a diagram of a simulated example of a phase-adjusting element 600 including a nanostructure array formed in a first region 610 corresponding to the first region 220 in FIG. 2A. Surrounding the first region 610 is the second region 620, corresponding to the second region 230 in FIG. 2A. FIG. 6B is an enlarged view of the portion of the phase-adjusting element 600 enclosed in box 6B in FIG. 6A, illustrating the nanostructures 630 formed in the first region 610. In the simulated example, 1000 nanostructures 630 are defined in the first region 610 and the nanostructures 630 are uniformly spaced (i.e., arranged in a regular pattern across the width 440 of the first region 610) with period of 300 nm and a duty cycle of 33.3% (i.e., each nanostructure is 100 nm wide and the spacing between adjacent nanostructures is 200 nm). The width 440 of the first region 610 is 300 μm, the same as the width 440 of the reference element. The material of the second region 620 is specified as BK7 with a refractive index of 1.517. As can be seen in FIG. 6B, and as discussed above, for the simulation, the water 450 entirely fills the space between the nanostructures 630 in the first region 610. Thus, the average refractive index for the first region can be calculated based on the refractive indexes of the BK7 (from which the nanostructures are made) and the water, and the duty cycle. From equation (3), to maintain the same phase shift of π as generated by the reference element, the depth 640 of the first region 610 is made to be 1.9 μm.

Figure 7:
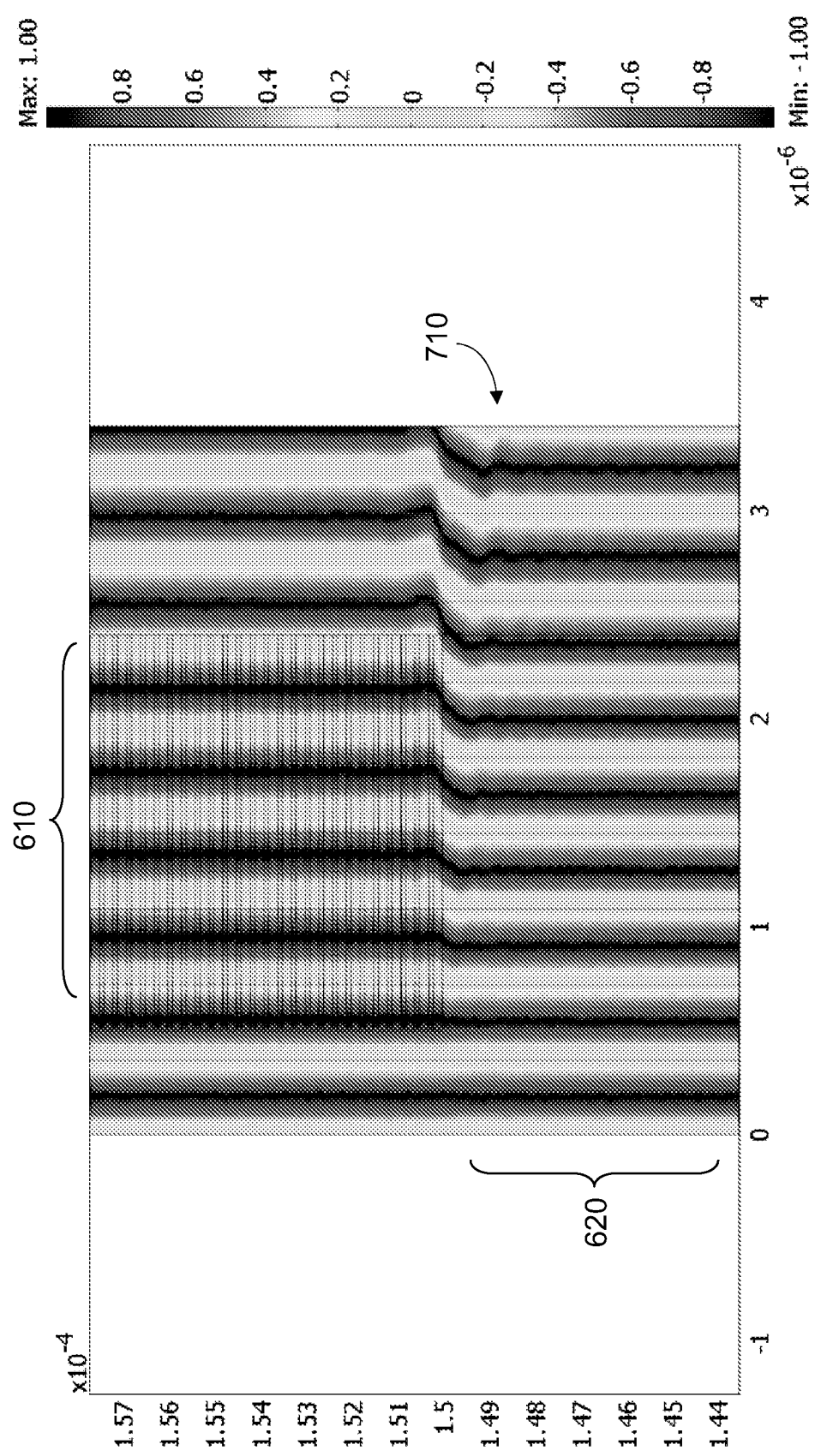
FIG. 7 is a diagram of the phase distribution of the perpendicular electric field along the simulated phase-adjusting element of FIG. 6A.

Reference is now made to FIG. 7 illustrating the phase distribution of the perpendicular electric field along the simulated phase-adjusting element 600. As can be seen with reference to FIG. 7, the phase of the electric field of the light in the first region 610 accumulates a linear phase shift along the depth of the first region 610 and maintains a plane wave phase front in both the first region 610 and the second region 620. The phase along the end of the first region 610 shows a phase difference of nearly π and the propagating field maintains the phase difference until the end of the simulated phase-adjusting element 600. Thus, the phase-adjusting element with the nanostructures 630 realizes an inverting phase shifter that produces a plane wave front with no diffraction caused by the nanostructures.

Figure 8A:
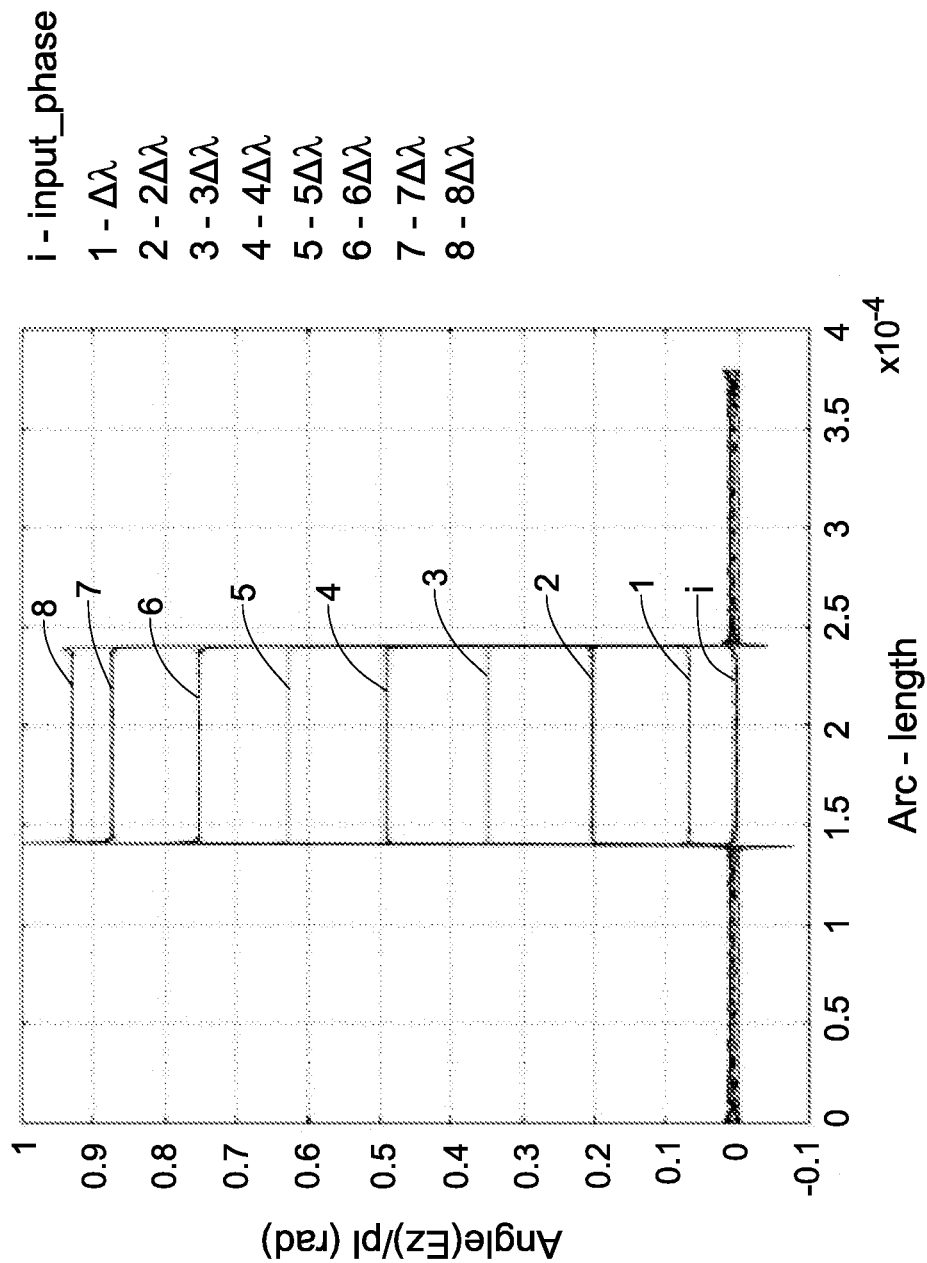
FIG. 8A is a diagram of a cross section of the phase along the direction of light propagation in the simulated phase-adjusting element of FIG. 6A for a nanostructure period of 300 nanometers and a nanostructure spacing of 200 nanometers.
Figure 8B:
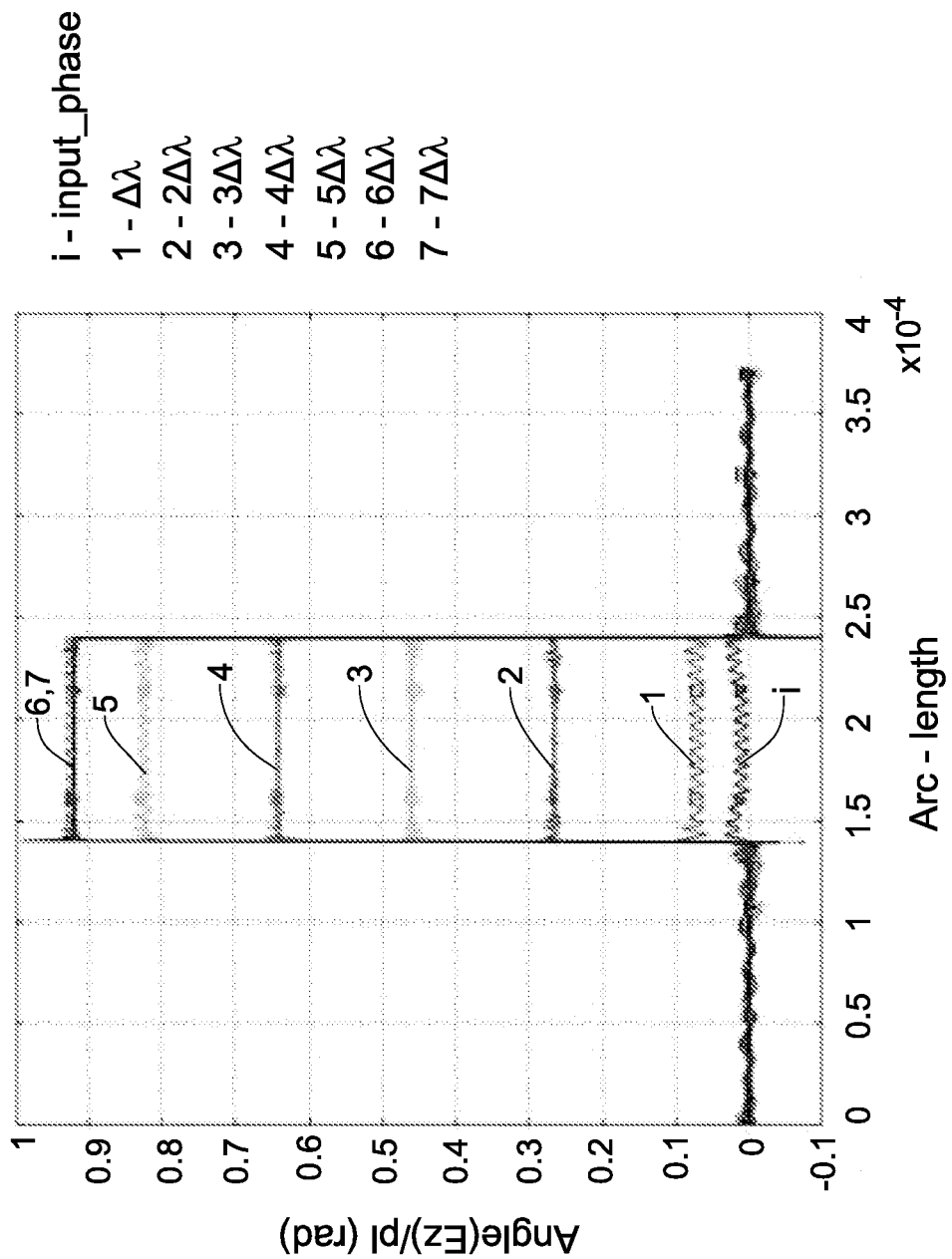
FIG. 8B is a diagram of a cross section of the phase along the direction of light propagation in the simulated phase-adjusting element of FIG. 6A for a nanostructure period of 350 nanometers and a nanostructure spacing of 250 nanometers.

Cross sections of the phase along the direction of light propagation are illustrated in FIGS. 8A and 8B. FIG. 8A illustrates the phase for the phase-adjusting element 610 discussed above having a spacing of 200 nm between the nanostructures. As can be seen with reference to FIG. 8A, the phase delay in the first region 610 shows a constant phase along the first region and the phase delay is linear with the light propagation inside the first region 610. FIG. 8B illustrates the phase for an example of the phase-adjusting element 610 with the nanostructure array having a period of 350 nm and a duty cycle of 28%. Thus, in the example of FIG. 8B, each nanostructure 630 is 100 nm wide and the spacing between adjacent nanostructures is 250 nm. The other dimensions and characteristics of the phase-adjusting element 610 are the same as discussed above. This increased spacing approaches the wavelength of the light in BK7. As can be seen with reference to FIG. 8B, the ripple in the phase implies a minor diffraction pattern caused by the larger spacing between the nanostructures 630. Accordingly, in order to avoid any type of diffraction, the spacing between the nanostructures may be kept under approximately a half wavelength (in free space) to account for the shortening of the wavelength of the light as it passes through the material of phase-adjusting element.

Referring again to FIG. 7, the visible distortion 710 in the phase at the edge of the first region 610 is caused by the sharp transition between the first region 610 which contains the nanostructures and the second region 620 due the difference in the refractive index between the two regions. This distortion may be reduced by "softening" the transition between the first region and the second region, for example, by implementing a graded change in the refractive index. In one embodiment, the spacing 280 between the nanostructures 260 is made variable with a largest spacing (and therefore lowest refractive index) toward a center of the first region 220 and a smallest spacing (and therefore highest refractive index, closest to the refractive index of the second region 230) toward the edges of the first region. By implementing a slowly increasing spacing 280 from the edges of the first region to the center of the first region, the average refractive index of the first region can be made to transition more gradually from that of the second region, reducing any edge distortion in the phase. It is to be appreciated that many variations in the spacing 280 between the nanostructures can be implemented. For example, the spacing 280 may be uniform, may increase from the edges of the first region 220 towards the center of the first region, may be "stepped" (i.e., groups of nanostructures may each have a specified spacing which may differ from group to group), may vary differently along different axes of the phase-adjusting element, or may be random.

According to one embodiment, the phase-adjusting element is substantially purely phase-affecting such that it alters the phase of the light passing therethrough, but does not substantially affect the amplitude of the light. In one example, the "surface roughness" due to the nanostructures 260 causes a scattering effect which causes a small amplitude change in the light. In other examples, however, the phase-adjusting element is configured to cause a substantial and controlled change in the amplitude of the light as well as the phase.

Having thus described several aspects of at least one embodiment, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

The invention claimed is:

1. A lens comprising a lens surface providing a refractive power, the lens surface comprising a plurality of concentric annular regions substantially entirely filled by an array of a plurality of optical elements formed on the surface thereof, with each adjacent pair of the plurality of concentric annular regions separated by a region devoid of optical elements, wherein each of the optical elements increases a thickness of the lens at the optical element, and wherein adjacent optical elements in each of the arrays are uniformly distributed and located less than 400 nm apart.

2. The lens of claim 1, wherein the lens surface comprises a central substantially circular region devoid of optical elements.

3. The lens of claim 1, wherein each of the optical elements increases a thickness of the lens at the optical element by at least 100 nm.

4. The lens of claim 1, wherein each of the optical elements is integral with the lens.

5. The lens of claim 1 wherein the plurality of concentric annular regions do not provide refractive optical power over the refraction of the lens.

6. The lens of claim 1 wherein the plurality of concentric annular regions do provide refractive optical power over the refraction of the lens.

7. The lens of claim 1, wherein the plurality of optical elements are dome-shaped.

8. The lens of claim 1, wherein the plurality of optical elements and the lens comprise the same material.

9. The lens of claim 1, wherein the plurality of optical elements and the lens comprise different materials.

10. The lens of claim 1, wherein the plurality of optical elements are optically transparent.

11. A spectacle lens comprising:
a lens comprising a lens surface;
a modulated relief on the lens surface, the modulated relief comprising a plurality of concentric annular regions having an array of a plurality of optical elements formed on the surface thereof, with each adjacent pair of the plurality of concentric annular regions separated by a region devoid of optical elements;
wherein:
each of the optical elements increases a thickness of the spectacle lens at the optical element;
adjacent optical elements in each of the arrays are uniformly distributed and located less than 400 nm apart; and
the spectacle lens is refractive.

12. The spectacle lens of claim 11, wherein the lens surface comprises a central substantially circular region devoid of optical elements.

13. The spectacle lens of claim 11, wherein each of the optical elements increases a thickness of the spectacle lens at the optical element by at least 100 nm.

14. The spectacle lens of claim 11, wherein each of the optical elements is integral with the lens.

15. The spectacle lens of claim 11, wherein the plurality of concentric annular regions do not provide refractive optical power over the refraction of the spectacle lens.

16. The spectacle lens of claim 11, wherein the plurality of concentric annular regions do provide refractive optical power over the refraction of the spectacle lens.

17. The spectacle lens of claim 11, wherein the plurality of optical elements are dome-shaped.

18. The spectacle lens of claim 11, wherein the plurality of optical elements and the lens comprise the same material.

19. The spectacle lens of claim 11, wherein the plurality of optical elements and the lens comprise different materials.

20. The spectacle lens of claim 11, wherein the plurality of optical elements are optically transparent.

* * * * *